United States Patent
Hendriks et al.

(10) Patent No.: US 11,571,180 B2
(45) Date of Patent: Feb. 7, 2023

(54) SYSTEMS PROVIDING IMAGES GUIDING SURGERY

(71) Applicant: KONINKLIJKE PHILIPS N.V., Eindhoven (NL)

(72) Inventors: Bernardus Hendrikus Wilhelmus Hendriks, Eindhoven (NL); Drazenko Babic, Best (NL); Jarich Willem Spliethoff, Utrecht (NL); Torre Michelle Bydlon, Melrose, MA (US); Grzegorz Andrzej Toporek, Boston, MA (US); Aleksandra Popovic, Boston, MA (US); Christian Reich, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 270 days.

(21) Appl. No.: 16/469,363

(22) PCT Filed: Dec. 18, 2017

(86) PCT No.: PCT/EP2017/083253
§ 371 (c)(1),
(2) Date: Jun. 13, 2019

(87) PCT Pub. No.: WO2018/109227
PCT Pub. Date: Jun. 21, 2018

(65) Prior Publication Data
US 2020/0015781 A1 Jan. 16, 2020

Related U.S. Application Data

(60) Provisional application No. 62/435,152, filed on Dec. 16, 2016.

(30) Foreign Application Priority Data

Jan. 19, 2017 (EP) .................................... 17152112

(51) Int. Cl.
*A61B 8/00* (2006.01)
*A61B 34/10* (2016.01)
(Continued)

(52) U.S. Cl.
CPC ............ *A61B 8/4245* (2013.01); *A61B 8/085* (2013.01); *A61B 34/10* (2016.02); *A61B 34/20* (2016.02);
(Continued)

(58) Field of Classification Search
CPC ....... A61B 8/4245; A61B 34/10; A61B 34/20; A61B 8/085; A61B 2034/2063;
(Continued)

(56) References Cited

U.S. PATENT DOCUMENTS 6,307,914 B1   10/2001   Kunieda
9,436,993 B1   9/2016   Stolka et al.
(Continued)

FOREIGN PATENT DOCUMENTS

JP   H01244740 A   9/1989
JP   2006055407 A   3/2006
(Continued)

OTHER PUBLICATIONS

C.R. Bard, Inc."Encor Enspire, Breast Biopsy System" Advertisement for Clinical Solutions, Originally Downloaded From https://www.crbard.com/biopsy in Mar. 2016.
(Continued)

*Primary Examiner* — Joel Lamprecht

(57) ABSTRACT

A system may generally comprise a tracking device, an ultrasound device and a processing unit. A position and orientation of the ultrasound device may be traceable by the tracking device. The processing unit may be configured (i) to receive 3D information of a region of interest in relation to a marker, with both the region of interest and the marker being located within a body, (ii) to determine the position of the marker relative to the ultrasound device based on an ultrasound image of the body including the marker, and (iii) to determine the position and orientation of the ultrasound
(Continued)

device relative to the tracking device. The system may further comprise a visualization device and the processing unit may further be configured to generate a visualization of the region of interest in relation to an outer surface of the body.

14 Claims, 4 Drawing Sheets

(51) Int. Cl.
*A61B 34/20* (2016.01)
*A61B 8/08* (2006.01)
*G06T 7/13* (2017.01)

(52) U.S. Cl.
CPC ........ *G06T 7/13* (2017.01); *A61B 2034/2063* (2016.02)

(58) Field of Classification Search
CPC ...... A61B 2090/371–373; A61B 90/39; A61B 2090/3908; G06T 7/13
See application file for complete search history.

(56) References Cited

U.S. PATENT DOCUMENTS

| | | |
|---|---|---|
| 2008/0298660 A1 | 12/2008 | Yamagata |
| 2011/0184291 A1 | 7/2011 | Okamura et al. |
| 2011/0246129 A1 | 10/2011 | Ishikawa |
| 2013/0218024 A1 | 8/2013 | Boctor et al. |
| 2016/0242855 A1* | 8/2016 | Fichtinger ...... A61B 17/320016 |

FOREIGN PATENT DOCUMENTS

| | | | |
|---|---|---|---|
| JP | 2013255658 A | 12/2013 | |
| JP | 2014221175 A | 11/2014 | |
| JP | 2015213627 A | 12/2015 | |
| JP | 2016202351 A | 12/2016 | |
| WO | 2015135985 A1 | 9/2015 | |
| WO | WO-2016064921 A1 * | 4/2016 | ............... G06T 7/62 |
| WO | 2016201341 A1 | 12/2016 | |
| WO | 2016201637 A1 | 12/2016 | |

OTHER PUBLICATIONS

Philips Ultrasound: Matrix Transducer, Advertisement for Ultrasound Transducer Technology, 10 Page Document, Originally Downloaded From https://www.usa.philps.com/healthcare/resources/feature-detail/xmatrix in Mar. 2016.
PCT/EP2017/083253 ISR and Written Opinion, dated Mar. 9, 2018, 29 pages.
Seow et al: "Sonogrpahic Visibility of Breast Tissue Markers:A Tissue Phantom Comparison Study"; AJUM, Nov. 2012, vol. 15(4), pp. 149-157.
Slomka et al.: "Multiple Iodine-125 Radioactive Seed Localizations:Single Institution Experience"; European Society of Radiology, 2015, pp. 1-24.

* cited by examiner

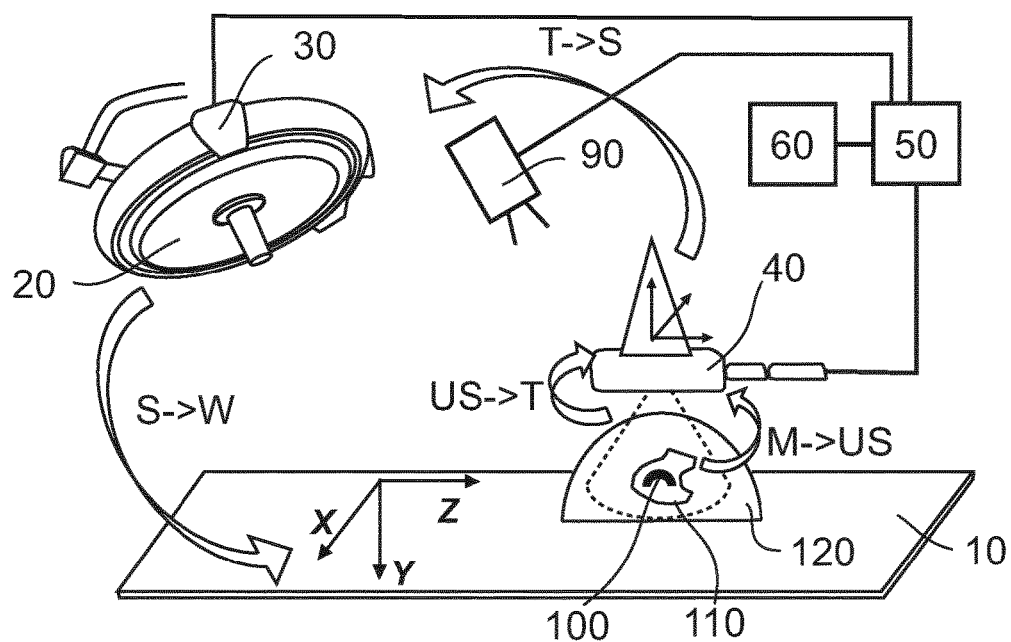
Fig. 1
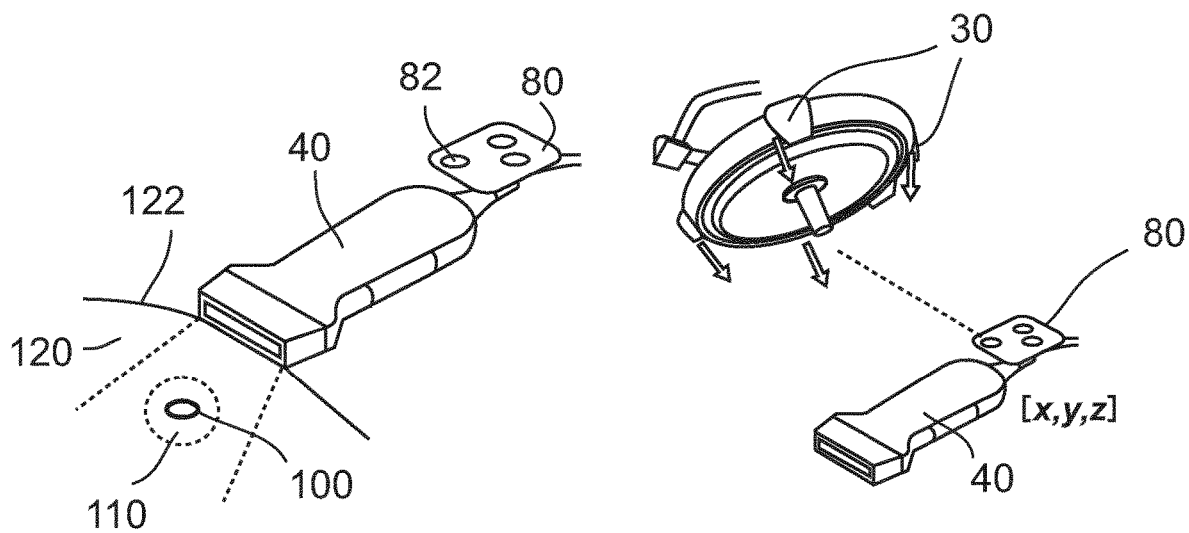
Fig. 2
Fig. 3

SYSTEMS PROVIDING IMAGES GUIDING SURGERY

CROSS-REFERENCE TO PRIOR APPLICATIONS

This application is the U.S. National Phase application under 35 U.S.C. § 371 of International Application No. PCT/EP2017/083253, filed on Dec. 18, 2017, which claims the benefit of U.S. Provisional Patent Application No. 64/435,152, filed on Dec. 16, 2016 and European Patent Application No. 17152112.3, filed on Jan. 19, 2017. These applications are hereby incorporated by reference herein.

FIELD OF THE INVENTION

The invention generally relates to aspects of assisting and guiding a physician in surgery. Particularly, the invention relates to a system providing visualizations which may help a physician in performing a surgical intervention.

BACKGROUND OF THE INVENTION

For example, surgical removal of breast tumours (e.g. lumpectomy) is one of the most frequently performed surgical resections with significant rate increase, due to the leading incidence and prevalence of the breast neoplasms. The clinical goal of the breast surgery is to remove the tumorous tissue entirely without leaving behind more than focally positive margins. Any trace of tumorous tissue left behind would potentially cause tumour recurrence and subsequent revision surgery. Radiotherapy is another treatment option where small microscopic portions left behind are treated by ionizing radiation.

A typical workflow for breast tumour resection starts with the inspection of the 2D images to make the excision plan. In case of non-palpable tumours or when patients are treated with neoadjuvant chemotherapy a marker is placed in the tumour for guidance during surgery. During surgery blue dye is injected to locate nearby lymph nodes that are inspected for the presence of tumour cells. The breast tumour is resected and visually inspected whether the resection is complete. The gold standard whether the resection is complete is by pathological analysis which takes typically 2 days.

Even though various pre-operative data sets are acquired (mammography, CT, MR, US), the surgeon has no reference from the imaging data when performing surgical tumour excision, apart from mental mapping based on the diagnostic scans and the anatomy being exposed to surgeon eyes. Once the patient is in the operating room the possibilities for imaging are limited, while the available pre-operative anatomical imaging often remains unemployed. During surgery, the surgeon must rely on visual and tactile feedback and tumour margins can often poorly be defined. Lack of the required real-time feedback leads to significant percentage of positive margins that require additional surgeries in later stage.

SUMMARY OF THE INVENTION

The problem to overcome by the invention is to provide visualization of tumour margins in relation to surgical instruments.

Ultrasound image guidance is used to guide for instance a biopsy needle towards a suspected lesion in a body during a biopsy procedure with high accuracy. Applying the same handheld ultrasound guidance during a tumour resection is much more difficult due to the high deformability of for example a breast and the limited visibility of the tumour boundary. As a result, it is very difficult to determine the position of a resection tool such as a surgical knife with respect to the tumour boundary.

A further object of the invention may be seen in providing a system reducing the risk for positive tumour margins. These and further objects are solved by the subject-matter of each of the independent claims. Further embodiments are described in the dependent claims, respectively.

In general, a system is proposed comprising a tracking device capable of tracking instruments, an ultrasound imaging system capable of imaging and thus tracking a marker in body tissue, wherein the ultrasound imaging system may be tracked by the tracking device, and a processing unit. Optionally, a surgical instrument is also trackable by the tracking device.

In an example, the processing unit may be capable of overlaying an ultrasound image with a pre-operative image of the tissue to be resected, based on the position of a marker which had already been placed in the tissue to be resected, wherein the pre-operative image includes the marker as well as the position of tumour boundaries.

The processing unit of the system in particular may be capable of calculating the position of the marker relative to the tracking device based on the position of the ultrasound system relative to the tracking device and on the position of the marker visible in the ultrasound image. Based on that calculation, an overlay of the pre-operative image may be presented to the physician, the image showing the tumour boundaries, for example relative to a surgical instrument.

In accordance with an embodiment, a system may generally comprise a tracking device, an ultrasound device and a processing unit. A position and orientation of the ultrasound device may be traceable by the tracking device. The processing unit may be configured (i) to receive 3D information of a region of interest in relation to a marker, with both the region of interest and the marker being located within a body, (ii) to determine the position of the marker relative to the ultrasound device based on an ultrasound image of the body including the marker, and (iii) to determine the position and orientation of the marker relative to the tracking device.

It will be understood that the marker is visible in an ultrasound image generated by the ultrasound device, thus allowing the determination of a position and orientation of the marker relative to the tracking device from the marker position relative to the ultrasound device and the tracked position and orientation of the ultrasound device itself.

According to an embodiment, the system may further comprise a visualization device and the processing unit may further be configured to generate a visualization of the region of interest in relation to an outer surface of the body.

According to an embodiment, the visualization device of the system comprises a projecting unit adapted to project the generated visualization onto a suitable surface. A suitable surface may be a white board, wherein the white board may be positioned so that a physician may look at the projection on the white board while performing any surgical procedure.

According to an embodiment, the white board showing a projection of the visualization may be positioned between the head of the physician and the hands of the physician so that the physician may have the impression to look onto the region of interest while treating the region of interest. The white board may be transparent allowing a view through the projected information onto a patient.

Alternatively, the projecting unit may project the visualization directly onto the outer surface of the body of the patient. It is noted that the visualization may comprise information of the patient, for example information relating to tumour boundaries. The information may also include any contour lines of body structures and/or of tumour structures.

The visualization may further include aspects of a camera image of the outer surface of the patient to facilitate an identification of structures of the patient. It will be understood that the visualization may in particular include a combination of information, not only the above mentioned information and visualization but also other information suitable to assist a physician in treating a patient. For example, the information may include an indication of an incision point/line to start a resection of a tumour and/or an indication of the region of interest including boundaries.

According to an embodiment, the system may include a vision device including both a tracking device and a projecting unit as described above.

According to another embodiment, the visualization device of the system may comprise a display adapted to actively show the generated visualization.

According to yet another embodiment, the visualization may be realized by a combination of a display showing for example a camera image of the outer surface of a patient, and of a projection onto that display, the projection illustrating for example structures being inside the body. In other words, an overlay of information may be realized by projecting information onto a display already showing other information. It will be understood that an overlay of information may also be generated by the processing unit and the display may show the already combined information in one image.

It is noted that the marker may comprise a structure allowing a determination of a 3D position and orientation of the marker based on an ultrasound image. A 3D position and orientation of the marker may also be determined based on at least two or multiple projections/images if a single ultrasound image is not sufficient to determine a 3D position of the marker. This may facilitate a determination of the spatial position and orientation of the marker relative to the ultrasound device. Such a determination may also or additionally improved by a 3D ultrasound device.

According to a further embodiment, the system may further comprise an instrument, wherein a position and orientation of the instrument is traceable by the tracking device, and wherein the generated visualization includes an indication of a relation of the instrument to the region of interest.

Furthermore, the system may comprise a camera for imaging the outer surface of the body. As mentioned above, the generated visualization of the region of interest may include an overlay onto an image generated by the camera.

According to an embodiment, the system may comprise an imaging device which may also be able to perform hyper/multispectral imaging. The imaging device may be capable to perform thermal imaging and/or PPG imaging.

According to yet another embodiment, the system may further comprise a probe that is trackable by the tracking device and is capable of tissue sensing based on at least one out of the group consisting of ultrasound, optical spectroscopy tissue sensing, impedance, THz sensing, temperature and PPG sensing.

The representation to the physician, i.e. the visualization, may provide an impression of the scale and/or relate both the tumour and the surgical instrument to other landmarks. Also additional fiducials may be placed on the patient's skin to make the representation more intuitive.

Another aspect of the invention concerns a computer program product. The computer program product may comprise sets of instructions for determining a position of a marker relative to a region of interest within a body based on first image data, determining a position of the marker relative to an ultrasound device based on second image data, wherein the second image data are ultrasound image data, determining a position and orientation of the ultrasound device based on data received from a tracking device, determining a spatial relation between the region of interest and the tracking device, generating a visualization indicating the position of the region of interest on the outer surface of the body.

Thus, the aim of the invention, i.e. providing images which may guide and/or at least help a physician to improve the results of a surgical intervention, may be implemented as computer software.

According to an embodiment, the computer program product may further comprise sets of instructions for generating an overlay of the visualization onto an image of the outer surface of the body received from a camera.

According to a further embodiment, the computer program product further comprises sets of instructions for controlling a projecting device, for determining boundaries of a region of interest, and for generating a visualization including a projection of the boundaries of the region of interest onto the outer surface of the body.

By means of a computer program product in accordance with an embodiment, real time processing of imaging data and tracking data allow for real time adaptation of visualizations to changes in the region of interest.

A corresponding computer program may preferably be loaded into a work memory of a data processor. The data processor or processing unit may thus be equipped to carry out at least a part of the method described herein. Further, the invention relates to a computer-readable medium such as a CD-ROM at which the computer program may be stored. However, the computer program may also be presented over a network like the World Wide Web and can be downloaded into the working memory of the data processor from such a network.

According to a further aspect, a method is provided comprising the steps of determining a region of interest inside a body relative to a marker based on a first image, wherein the first image is a pre-operative image, determining a spatial position of the marker relative to an ultrasound device based on a second image, wherein the second image is generated by the ultrasound device, determining a spatial position and orientation of the ultrasound device, generating an indication of a spatial position of the region of interest in relation to an outer surface of the body.

According to an embodiment, the method may further comprise the step of providing a projection of guiding indications onto the outer surface of the body.

According to an embodiment, the method may further comprise the steps of determining a spatial position and orientation of an instrument, and generating an indication of a spatial position of the instrument in relation to the region of interest.

According to a further embodiment, the method does not include any step of treatment of a human or animal body by surgery. For example, the method does not include a step of inserting the marker into the region of interest. Although the visualization may be generated in real time and in parallel to a surgical procedure, the method does not comprise a step of any incision into tissue and also not any step of resection of tissue, in particular of tumour tissue.

It has to be noted that embodiments are described with reference to different subject-matters. In particular, some embodiments are described with reference to method type claims (computer program) whereas other embodiments are described with reference to apparatus type claims (system). However, a person skilled in the art will gather from the above and the following description that unless other notified in addition to any combination of features belonging to one type of subject-matter also any combination between features relating to different subject-matters is considered to be disclosed with this application.

The aspects defined above and further aspects, features and advantages of the present invention may also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

FIG. 1 illustrates a system providing images according to an embodiment.

FIG. 2 shows an ultrasound device imaging a marker.

FIG. 3 illustrates a tracking of an ultrasound device.

The illustration in the drawings is schematically only and not to scale. It is noted that similar elements are provided with the same reference signs in different figures, if appropriate.

DETAILED DESCRIPTION OF EMBODIMENTS

Figure 4:
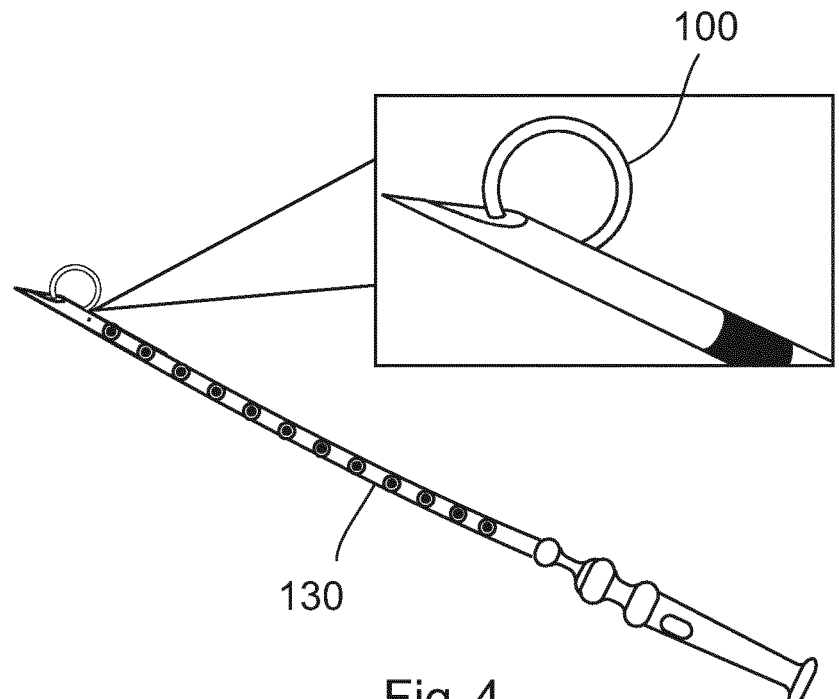
FIG. 4 shows a device suitable for placing a marker in a region of interest.

FIG. 1 illustrates a system in accordance with an embodiment. FIGS. 2 and 3 show elements of the system in more detail. Shown in FIG. 1 is a patient couch or table 10 and an operation light 20, which are typically present in an operation theater. The system according to an embodiment described herein comprises a tracking device 30, an ultrasound device 40, a processing unit 50 and a display 60 as a visualization device. Schematically visualized in FIG. 1 is a marker 100 placed within a region of interest 110 inside a body 120.

Optionally, the system may comprise at least one camera 90. The camera 90 may be a video camera for imaging the outer surface of the body or may additionally or alternatively be a camera allowing imaging outside the visible spectrum of light. Images generated by any of these cameras may be used to generate an overlay image of the camera image with an ultrasound image from the ultrasound device and/or with a pre-operatively generated image. The position and orientation of the camera relative to a world coordinate system, i.e. to a fixed space coordinate system, or at least to another element of the system like the tracking device may be known. The camera 90 may for example be integrated into an operation or surgical light.

The tracking device 30 may be arranged at the operation or surgical light 20 so that the tracking device may observe in particular the field of view of the operation light. At that arrangement, the spatial position and orientation of the tracking device can be considered as known, i.e. may be determined in fixed relation to the operation light and thus in relation to a world coordinate frame.

The tracking device 30 may contain at least one, preferably two or more cameras capable of 3D tracking of instruments, for example using an optical tracer plate 80 attached to an instrument. Alternatively or in addition, suitable marker patterns on the instrument itself may be used, which are identifiable in the camera images. On the basis of two or more cameras, the accuracy may be increased by means of triangulation.

A camera of the tracking device 30 may also be configured as described above with respect to optional camera 90. In this example, a stream of video images from such camera is used both for purposes of tracking and imaging the outer surface of the body. The camera position and orientation then correspond to that of the tracking device. Thus, a spatial relationship between video images of the tracking device cameras, the ultrasound device, the marker, and thereby the 3D information such as pre-operative 3D imaging like MRT or CT, is known. As a result, video images from tracking device cameras may be used in the overall visualization with relative ease.

A processing unit 50 may be adapted to determine the parallax of the objects in the images of the tracking device and translating these in a position relative to the tracking device and thus to a fixed coordinate system. The system may also contain a hyperspectral camera capable of monitoring the body in different spectral wavelength bands. The system may, in addition to display 60 or as an alternative thereto, also comprise a projecting device 70 capable of projecting information onto the patient. The system may also contain a thermal, PPG camera.

As can better be seen in FIG. 2, the ultrasound device 40 may be arranged in contact with an outer surface 122 of the body 120, so that the region of interest 110 within that body can be imaged by the ultrasound device 40. The ultrasound device may be an ultrasound probe capable of performing 3D ultrasound imaging. The ultrasound device 40 may comprise a tracer plate 80 with a plurality of elements 82 which are appropriate to be determined by a camera of the tracking device. For example, the elements 82 may be spheres being arranged in a unique way relative to each other so that an orientation of the tracer plate 80 may be determined by means of one tracking camera. It is noted that both orientation and translation (6DOF) may be determined using a camera utilizing 2D-3D registration (such as RANSAC algorithm).

Otherwise, there may be more than one tracking camera allowing a kind of triangulation of the position of the elements 82 and thus of the tracer plate 80, and thus of the ultrasound device 40, relative to the tracking device 30. FIG. 3 shows an embodiment including a plurality of tracking cameras 30 for identifying a 3D position and orientation of the tracer plate 80 at the ultrasound device 40.

A position of a region of interest, for example a tumor, may be determined in the world coordinate frame by the following steps. A marker 100 that is already placed in the tumor before surgery is imaged by an ultrasound probe 40. Therefore the position of the marker can be determined in relation to the ultrasound probe (M→US in FIG. 1). The position of the marker will be known in the pixel space of the ultrasound image. A mapping from the pixel space to the probe space is performed to determine a position of the marker with respect to the ultrasound probe. The ultrasound probe may have a tracer plate 80 attached that is tracked by the tracking device 30 of the system. Alternatively or in addition, it is provided with suitable marker patterns identifiable in, for example, video images generated by cameras in the tracking device 30.

Therefore the position of the elements 82 of the tracer plate 80 can be determined in relation to the tracking device (US→T and T→S in FIG. 1). When a surgical instrument shall be tracked by the system, the relative position of the instrument with respect to the marker in the region of interest may also be determined. The position of the tracking device relative to a fixed space coordinate (S→W in FIG. 1) may finally be determined, which allows for a coordinate basis in particular when more than one instrument or ultrasound probe is tracked.

FIG. 4 is an illustration of an O-twist marker 100 and of an introducer needle 130 being adapted to insert the marker in a region of interest. O-twist markers may be used to mark for example breast lesions that might not be visible on imaging after completion of neoadjuvant chemotherapy.

Figure 5:
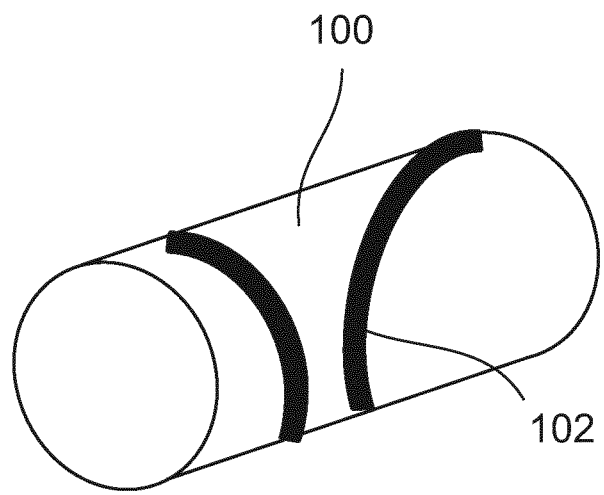
FIG. 5 shows a marker in accordance with an embodiment.

FIG. 5 shows another marker 100, i.e. a cylindrical marker with characteristic rims 102 on the outer surface facilitating a determination of an orientation of the marker based on ultrasound imaging. The rims in the marker 100 may allow recognition of an orientation of the marker in three dimensions (6 degrees of freedom). As finally a position of the region of interest inclusive boundaries shall be determined in relation to an instrument, the marker and a relative position of the marker inside the region of interest should be known, for example as determined based on 3D information such as pre-operative 3D imaging like MRT or CT.

Besides the markers shown in FIGS. 4 and 5, radioactive seeds may be used for localization. Such markers may be well visible under both X-ray as well as ultrasound. They may have an elongated cylindrical shape.

It will be understood that the marker will likely be removed with the tumor during surgery. Otherwise, ultrasound markers may be used being biodegradable. For example, polylactic acid/polyglycolic acid (PLA/PGA) pallets provide 4-6 weeks of ultrasound visibility and are reabsorbed in approximately 12 weeks. These markers could be placed in areas of tissue that may not be resected.

Another set of markers may include at least two rigid markers that are connected by a flexible wire with fixed length. When such markers are placed in the body, relative movements of the markers may be an indication for the deformation of the body tissue. There may be other marker types.

According to a further aspect, a use of a hyperspectral or multispectral camera is proposed, wherein the term "hyperspectral imaging" as used herein refers to collecting and processing information from across a range of the electromagnetic spectrum extending beyond the visible range, and the term "multispectral imaging" as used herein refers to capturing image data at specific frequencies across the electromagnetic spectrum. The wavelengths may be separated by filters or by the use of instruments that are sensitive to particular wavelengths, i.e. multiple spectra are used, which is the reason for the term "multispectral imaging". This may include light from frequencies beyond the visible light range, such as infrared, which then may also be defined by the term "hyper" of the aforementioned term "hyperspectral imaging".

Spectral (multispectral or hyperspectral) imaging may allow extraction of additional information from an image, especially information that the human eye fails to capture with its receptors for red, green and blue. According to an embodiment, the camera 90 may be a hyperspectral or multispectral filter-wheel camera for hyperspectral or multispectral imaging with a spectral range of 400 to 1000 nm (nanometer) or from 1000 to 1700 nm or from 500 to 1700 nm, with various, for instance 6 or 8 or even more interchangeable filters, with a charge-coupled device CCD with a resolution of 1392×1040 pixels or physical points in a raster image, or, for instance with an Indium gallium arsenide (InGaAs) or any other semiconductor sensor with a resolution of 640×512 pixels, or with a sensor with any other pixel resolution. The wavelength bands for camera 90 may be in the visible or non-visible light spectrum comprising several wavelength bands as for instance:

(1) Blue: 0.450-0.520 µm (micrometer)
(2) Green: 0.515-0.600 µm
(3) Red: 0.60-0.69 µm
(4) Visible: 0.45-0.7 µm
(5) Infrared: 0.7-1.0 µm
(6) Near infrared: 1.0-3.0 µm
(7) Mid infrared: 3.0-50.0 µm
(8) Far infrared: 50.0-1000.0 µm Extending the wavelength enables that the tissue contrast between several structures can be enhanced.

As mentioned above, it may be of interest to at least partially fuse images from different image sources. For example, an overlay of information extracted from one image with information from another image may be of interest. To achieve such combined images, the images must be registered.

A registration between for example intraoperative 3D ultrasound volume images and preoperative 2D mammography images may allow a display of tumor margins in ultrasound images. The ultrasound transducer may be positioned approximately perpendicular to mammography system to allow same or similar imaging planes to be observed. In the first step of a procedure, each ultrasound slice (taken from ultrasound volume) is processed to identify and segment the marker in 2D. This can be done using thresholding or active contour gradient based segmentation. Once the marker is identified and its shape segmented, the shape is matched and compared to the marker shape from a mammography image. A cost function is applied measuring the similarity between two observed shapes. This cost function can be implemented using any known method(s) including graph matching, Housdorff distance, and feature based methods (e.g. using salient points of the marker). After the volume sweep is complete, the slice with the lowest cost function can be assumed to most closely resemble the mammography projection which allows display of tumor margins in that slice. To improve accuracy of this method, an electronic steering of the ultrasound beam can be added to the slice sweep.

Furthermore, the marker shape may be compared between projection-like composite images of ultrasound (fusion of multiple ultrasound slices from the same volume) from electronically steered beam and mammography, to mimic projection images of X-ray.

Further, the overlay of tumor margins in the ultrasound slice can be used to initialize segmentation of an ultrasound volume: the margins are used to learn acoustic properties of the tumor (e.g. modelled using Gaussian mixture model or similar) and initialize segmentation algorithm (e.g. active contours or level set). Further, 3D ultrasound can be registered to digital breast tomosynthesis (DBT) images. DBT images are typically not reconstructed due to limited rotation angles during the image acquisition. This limitation can be overcome by registering to ultrasound using the method described above. The result of this registration is based on a known shape of the marker in each X-ray image and a known shape of the marker from missing rotations that can be replaced with shape from ultrasound images. Using this information, a full reconstruction of the 3D volume from DBT can be achieved using back-projection algorithms known in the art.

Figure 6:
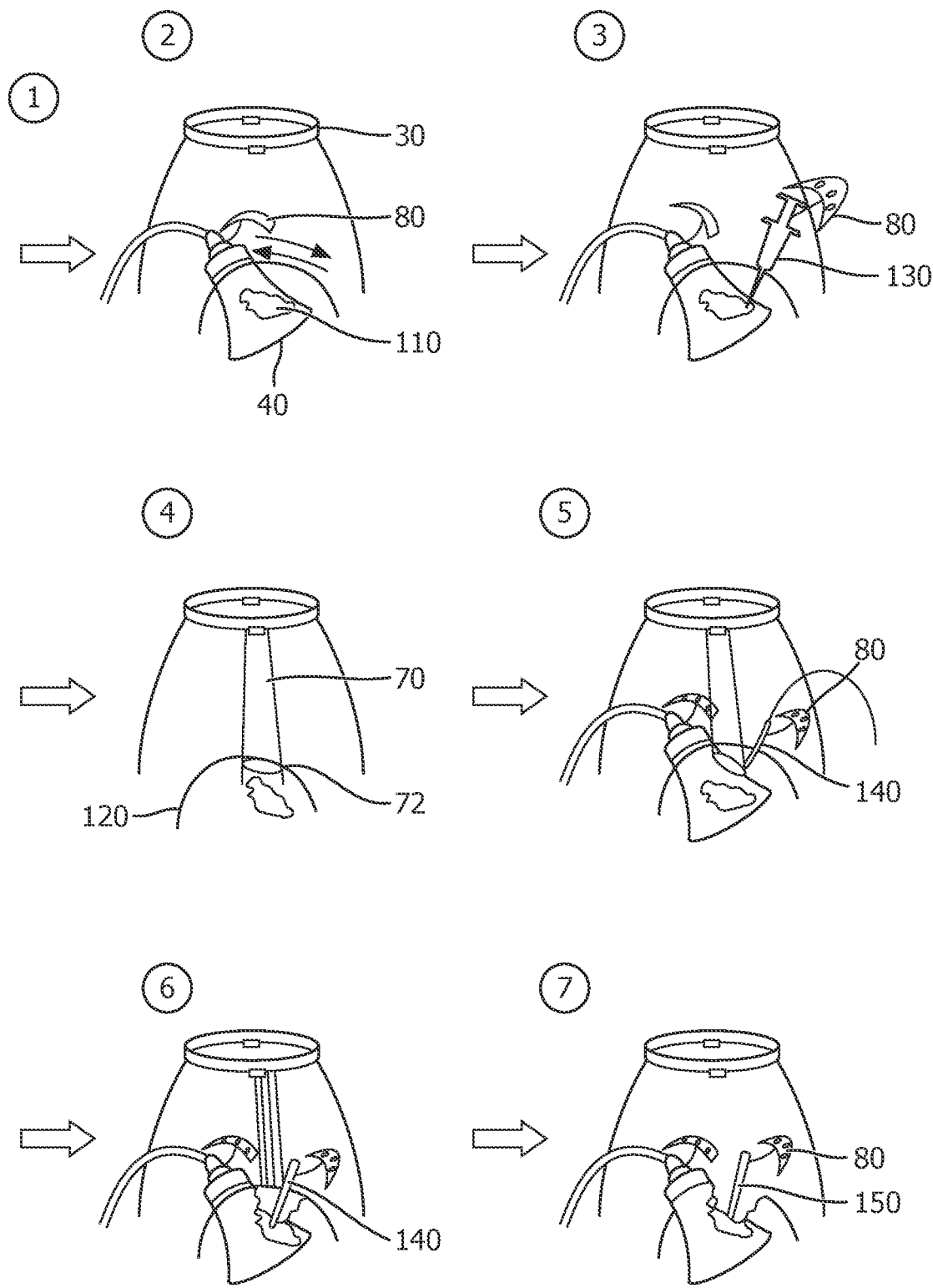
FIG. 6 illustrates a sequence of instances in which a system according to an embodiment of the invention can be advantageously used.

FIG. 6 shows a sequence of instances during a tumor resection as an example of an application of the system for providing images guiding in a surgical procedure. The embodiment of the system shown in FIG. 6 includes an ultrasound device 40 with a tracer plate 80, a tracking device 30 and a projecting device 70. Furthermore, the system comprises an introducer 130 for inserting a marker into the region of interest 110, wherein that introducer 130 also has a tracer plate 80. The system further comprises an instrument 140 for resecting tissue, in particular tissue in the region of interest 110, wherein the instrument 140 is also provided with a tracer plate 80. The system also comprises a probe 150 with a tracer plate 80, which probe 150 may be adapted for tissue inspection. With such a system, the following scenario is possible.

After taking a preoperative image with an echogenic marker visible in the image (step 1), a 3D lesion is localized based on the position of the echogenic marker with an ultrasound probe 40 that is tracked by the tracking system 30 (step 2), additional markers may be placed in the tumor 110 by means of an introducer 130 for enhanced tracking with ultrasound (step 3), a lesion back projection 72 is generated as a visualization on body 120 by projector 70 (step 4), tumor may be resected with an instrument 140 a position of which is determined relative to the tumor margin visible on the pre-operative image (step 5), the intervention may additionally be guided based on hyperspectral, thermal, PPG imaging (step 6) and the resection area may be inspected with tissue sensing (ultrasound, optical spectroscopy, impedance) by means of a tracked probe 150 (step 7).

Figure 7:
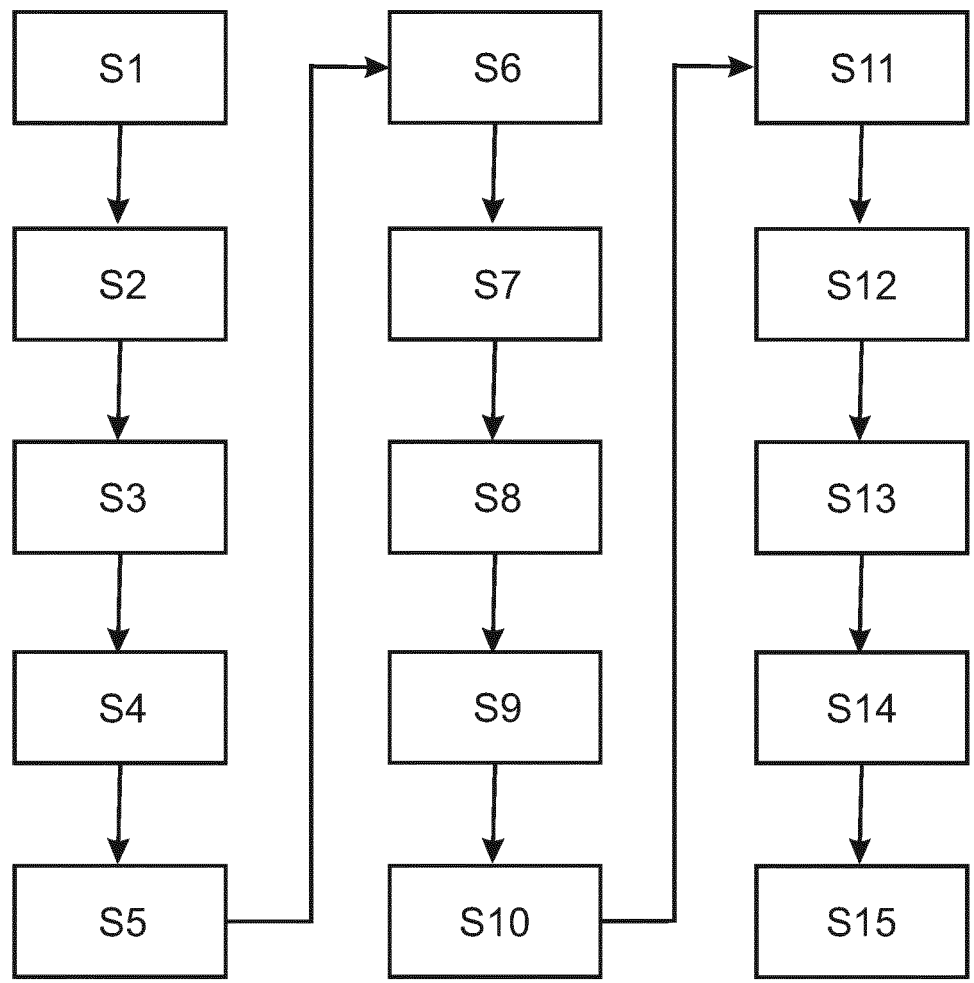
FIG. 7 is a flow chart illustrating steps of a method according to an embodiment.

The flow-chart in FIG. 7 illustrates the principle of the steps performed in accordance with an embodiment described herein. It will be understood that the steps described, are major steps, wherein these major steps might be differentiated or divided into several sub-steps. Furthermore, there might be also sub-steps between these major steps.

As a first aspect, a position of the tumor may be determined in the World coordinate frame. This is achieved by placing a marker in a region of interest, for example a tumor (step S1), by locating and tracking the marker with an ultrasound probe (step S2), by locating the ultrasound probe with the tracking device (step S3), by receiving marker location data and ultrasound images directly from an ultrasound console to a processing unit (step S4) and by receiving the ultrasound probe location data from the tracking device to the processing unit (step S5). Finally, the processing unit may determine positional relation between the marker, the ultrasound probe and the tracking device (step S6).

As a further aspect, processed information can be generated and provided which may be useful (but not necessary) as guidance for an intervention. In step S7, an overlay of a pre-operative image including tumor margins with the marker may be generated. Alternatively or in addition, real-time ultrasound image data (step S8) and/or hyperspectral image data (step S9) and/or video camera image data (step S10) may be registered with the pre-operative image data, with the marker as main element for the registration, i.e. as a kind of an anchoring element in the different images. Then, a visualization may be generated based on the image data (step S10) and shown as a projection and/or on a display (step S11). For example, a location of the marker may be projected onto the patient in step S11.

Furthermore, a position and orientation of an interventional instrument may be tracked in step S12 and a relation of the same with respect to boundaries of the region of interest may be determined (step S13). In step S14, a representation of the instrument may be added in the visualization. The visualization may be improved with tissue feedback information from the tip of the instrument (step S15). It is noted that the available real-time images allow an adaptation of the generated visualization to any progress of the intervention.

While the invention has been illustrated and described in detail in the drawings and foregoing description, such illustration and description are to be considered illustrative or exemplary and not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS 10 patient couch
20 operation light
30 tracking device
40 ultrasound device
50 processing unit
60 display
70 projecting device
72 projection
80 tracer plate
82 traceable elements
90 camera
100 marker
102 rim
110 region of interest
120 body
122 outer surface of body
130 introducer
140 instrument
150 probe

The invention claimed is:

1. A system for providing images guiding surgery, comprising:
an ultrasound device configured to generate, during a surgical procedure, an ultrasound image that includes a marker located within a body;
a tracking device configured to track in a fixed coordinate space (i) position of the ultrasound device and (ii) position of a surgical instrument within the body;
a processor configured to:
receive a pre-operative image of a region of interest in relation to the marker within the body, determine a position of the marker relative to the ultrasound device based on the ultrasound image, determine a position of the marker in the fixed coordinate space of the tracking device based on (i) the determined position of the marker relative to the ultrasound device and (ii) the tracked position of the ultrasound device in the fixed coordinate space of the tracking device, and determine position of the region of interest in relation to the tracked position of the surgical instrument, in the fixed coordinate space based on (a) the determined position of the marker in the fixed coordinate space and (b) the relation of the marker and region of interest in the pre-operative image; and a display configured to display the determined position of the region of interest in relation to the tracked position of the surgical instrument.

2. The system of claim 1, wherein the processor is further configured to generate a visualization of the region of interest in relation to an outer surface of the body.

3. The system of claim 2, wherein the generated visualization of the region of interest includes a projection of boundaries of the region of interest.

4. The system of claim 2, wherein the display is configured to show the generated visualization.

5. The system of claim 2, further comprising a projector adapted to project the generated visualization.

6. The system of claim 1, wherein the marker comprises a structure allowing a determination of a 3D position and orientation of the marker based on the ultrasound image.

7. The system of claim 2, further comprising a camera for imaging the body including the region of interest, wherein the generated visualization of the region of interest includes an overlay of image information from different images.

8. The system of claim 1, further comprising a hyperspectral or multispectral camera for imaging the region of interest.

9. A non-transitory computer-readable storage medium having stored a computer program comprising instructions, the instructions, when the computer program is executed by a processor, cause the processor to:

receive, from an ultrasound device during a surgical procedure, an ultrasound image that includes a marker within a body;

receive a pre-operative image of a region of interest in relation to the marker within the body;

determine a position of the marker relative to the ultrasound device based on the ultrasound image;

determine a position of the marker in a fixed coordinate space of a tracking device based on (i) the determined position of the marker relative to the ultrasound device and (ii) a position of the ultrasound device tracked by the tracking device in the fixed coordinate space;

determine position of the region of interest, in relation to a position of a surgical instrument tracked by the tracking device, in the fixed coordinate space based on (a) the determined position of the marker in the fixed coordinate space and (b) the relation of the marker and region of interest in the pre-operative image; and display the determined position of the region of interest in relation to the tracked position of the surgical instrument.

10. The non-transitory computer-readable storage medium of claim 9, wherein the instructions, when the computer program is executed by the processor, further cause the processor to generate an overlay of the visualization onto an image of an outer surface of the body received from a camera.

11. The non-transitory computer-readable storage medium of claim 9, wherein the visualization includes a projection of boundaries of the region of interest onto the outer surface of the body.

12. A method comprising:

receiving, from an ultrasound device during a surgical procedure, an ultrasound image that includes a marker within a body;

receiving a pre-operative image of a region of interest in relation to the marker within the body;

determining a position of the marker relative to an ultrasound device based on the ultrasound image;

determining a position of the marker in a fixed coordinate space of a tracking device based on (i) the determined position of the marker relative to the ultrasound device and (ii) a position of the ultrasound device tracked by the tracking device in the fixed coordinate space;

determining position of the region of interest, in relation to a position of a surgical instrument tracked by the tracking device, in the fixed coordinate space based on (a) the determined position of the marker in the fixed coordinate space and (b) the relation of the marker and region of interest in the pre-operative image; and display the determined position of the region of interest in relation to the tracked position of the surgical instrument.

13. The method of claim 12, further comprising providing a projection of an indication of the region of interest onto an outer surface of the body.

14. The method of claim 12, further comprising generating an indication of a spatial position of the surgical instrument in relation to the region of interest.

* * * * *